US009440081B2

(12) United States Patent
Demmer et al.

(10) Patent No.: US 9,440,081 B2
(45) Date of Patent: *Sep. 13, 2016

(54) METHODS FOR PROMOTING INTRINSIC ACTIVATION IN SINGLE CHAMBER IMPLANTABLE CARDIAC PACING SYSTEMS

(71) Applicant: Medtronic, Inc., Minneapolis, MN (US)

(72) Inventors: Wade M Demmer, Coon Rapids, MN (US); Karen J Kleckner, New Brighton, MN (US); Paul A Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/716,463

(22) Filed: May 19, 2015

(65) Prior Publication Data

US 2015/0360034 A1    Dec. 17, 2015

Related U.S. Application Data

(63) Continuation of application No. 14/305,722, filed on Jun. 16, 2014, now Pat. No. 9,042,984, which is a continuation of application No. 13/932,782, filed on Jul. 1, 2013, now Pat. No. 8,755,884, which is a continuation of application No. 13/192,706, filed on Jul. 28, 2011, now Pat. No. 8,478,407.

(51) Int. Cl.
*A61N 1/365* (2006.01)

(52) U.S. Cl.
CPC ....... *A61N 1/36514* (2013.01); *A61N 1/36507* (2013.01); *A61N 1/36592* (2013.01)

(58) Field of Classification Search
CPC .... A61N 1/365; A61N 1/3627; A61N 1/362; A61N 1/36592; A61N 1/36514; A61N 1/36585; A61N 1/3702; A61N 1/36507
See application file for complete search history.

(56) References Cited

U.S. PATENT DOCUMENTS

| 4,428,378 A | 1/1984 | Anderson et al. |
| 5,265,601 A | 11/1993 | Mehra |

(Continued)

FOREIGN PATENT DOCUMENTS

| CN | 1235651 C | 7/2001 |
| CN | 101641132 B | 11/2012 |

(Continued)

OTHER PUBLICATIONS (PCT/US2012/048041) PCT Notification of Transmittal of the International Search Report and the Written Opinion of the International Searching Authority.

(Continued)

*Primary Examiner* — Rex R Holmes
(74) *Attorney, Agent, or Firm* — Evans M. Mburu; Stephen W. Bauer

(57) ABSTRACT

Cardiac pacing methods for an implantable single chamber pacing system, establish an offset rate for pacing at a predetermined decrement from either a baseline rate (i.e. dictated by a rate response sensor), or an intrinsic rate. Pacing maintains the offset rate until x of y successive events are paced events, at which time the offset rate is switched to the baseline rate for pacing over a predetermined period of time. Following the period, if an intrinsic event is not immediately detected, within the interval of the offset rate, the rate is switched back to baseline for pacing over an increased period of time. Some methods establish a preference rate, between the offset and baseline rates, wherein an additional criterion, for switching from the offset rate to the baseline rate, is established with respect to the preference rate.

13 Claims, 6 Drawing Sheets

(56) References Cited

U.S. PATENT DOCUMENTS

| | | | |
|---|---|---|---|
| 5,284,491 A * | 2/1994 | Sutton | A61N 1/365 607/17 |
| 5,320,643 A | 6/1994 | Roline et al. | |
| 5,350,401 A | 9/1994 | Levine | |
| 5,372,607 A | 12/1994 | Stone et al. | |
| 5,374,281 A | 12/1994 | Kristall et al. | |
| 5,447,525 A | 9/1995 | Powell et al. | |
| 5,480,414 A | 1/1996 | Stroebel et al. | |
| 5,522,859 A | 6/1996 | Stroebel et al. | |
| 5,861,007 A | 1/1999 | Hess et al. | |
| 5,873,898 A | 2/1999 | Hemming et al. | |
| 5,957,957 A | 9/1999 | Sheldon | |
| 6,122,546 A | 9/2000 | Sholder et al. | |
| 6,129,745 A | 10/2000 | Sun et al. | |
| 6,134,473 A | 10/2000 | Hemming et al. | |
| 6,141,586 A | 10/2000 | Mower | |
| 6,144,881 A | 11/2000 | Hemming et al. | |
| 6,772,005 B2 | 8/2004 | Casavant et al. | |
| 7,130,683 B2 | 10/2006 | Casavant et al. | |
| 7,177,683 B2 | 2/2007 | Belk | |
| 7,218,965 B2 | 5/2007 | Casavant et al. | |
| 7,248,924 B2 | 7/2007 | Casavant et al. | |
| 7,738,959 B2 | 6/2010 | Manrodt et al. | |
| 7,881,793 B2 | 2/2011 | Betzold et al. | |
| 7,937,148 B2 | 5/2011 | Jacobson | |
| 8,478,407 B2 * | 7/2013 | Demmer | A61N 1/36507 607/17 |
| 8,543,204 B2 | 9/2013 | Demmer et al. | |
| 8,626,294 B2 | 1/2014 | Sheldon et al. | |
| 8,755,884 B2 * | 6/2014 | Demmer | A61N 1/35507 607/17 |
| 8,942,806 B2 | 1/2015 | Sheldon et al. | |
| 9,042,984 B2 * | 5/2015 | Demmer | A61N 1/36507 607/17 |
| 2003/0208241 A1 | 11/2003 | Bradley et al. | |
| 2004/0064162 A1 | 4/2004 | Manrodt et al. | |
| 2004/0116973 A1 | 6/2004 | Ohman | |
| 2004/0172082 A1 | 9/2004 | Ferek-Petric | |
| 2007/0088397 A1 | 4/2007 | Jacobson | |
| 2008/0221636 A1 | 9/2008 | Pastore et al. | |
| 2009/0306486 A1 | 12/2009 | Li et al. | |
| 2009/0306586 A1 | 12/2009 | Ross et al. | |

FOREIGN PATENT DOCUMENTS

| | | |
|---|---|---|
| EP | 0 313 881 A2 | 5/1989 |
| EP | 0311019 A1 | 12/1989 |
| EP | 0624384 A1 | 11/1994 |
| EP | 1302217 A2 | 4/2003 |
| EP | 1291038 A2 | 12/2003 |
| WO | WO 96/15828 A1 | 5/1996 |
| WO | WO 2006/079010 A1 | 7/2006 |
| WO | 2007047681 A2 | 4/2007 |

OTHER PUBLICATIONS

Chinese Office Action, mailed Nov. 28, 2014, 8 pages.
Chinese Office Action, mailed Nov. 28, 2014, English translation, 12 pages.
"Initial Clinical Experience with a Single Pass VDDR Pacing System", by Chu-Pak Lau et al., Pacing and Clinical Electrophysiology, November, Part II, 1992, vol. 15, pp. 1894-1900.
(PCT/US20121068974) PCT Notification of Transmittal of the International Search Report and the Written Opinion of the International Searching Authority.

* cited by examiner

METHODS FOR PROMOTING INTRINSIC ACTIVATION IN SINGLE CHAMBER IMPLANTABLE CARDIAC PACING SYSTEMS

RELATED APPLICATION

This application is a continuation of U.S. patent application Ser. No. 14/305,722, filed Jun. 16, 2014 (now issued as U.S. Pat. No. 9,042,984) entitled "METHODS FOR PROMOTING INTRINSIC ACTIVATION IN SINGLE CHAMBER IMPLANTABLE CARDIAC PACING SYSTEMS", which is a continuation of U.S. patent application Ser. No. 13/932,782, filed Jul. 1, 2013 (now issued as U.S. Pat. No. 8,755,884) entitled "METHODS FOR PROMOTING INTRINSIC ACTIVATION IN SINGLE CHAMBER IMPLANTABLE CARDIAC PACING SYSTEMS", which is a continuation of U.S. patent application Ser. No. 13/192,706, filed Jul. 28, 2011 (now issued as U.S. Pat. No. 8,478,407) entitled "METHODS FOR PROMOTING INTRINSIC ACTIVATION IN SINGLE CHAMBER IMPLANTABLE CARDIAC PACING SYSTEMS", all of which are herein incorporated by reference in their entirety.

TECHNICAL FIELD

The present invention pertains to cardiac pacing methods and more particularly to pacing methods that promote intrinsic activation of ventricular depolarization to preserve natural conduction and increase system efficiency in single chamber implantable cardiac pacing systems.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of cardiac pacing systems that are wholly contained within a relatively compact package for implant in close proximity to the pacing site, for example, within the right ventricle (RV) of the heart. With reference to FIGS. 1A-B, such a system 100 is illustrated, wherein pace/sense electrodes 111, 112 are formed on an exterior surface of a capsule 101 that hermetically contains a pulse generator 103 (shown in FIG. 1B via a block diagram). FIG. 1A further illustrates tine members 115 mounted to an end of capsule 101, in proximity to electrode 111, in order to secure electrode 111 against the endocardial surface of RV, and electrode 112 offset distally from electrode 111. Capsule 101 is preferably formed from a biocompatible and biostable metal such as titanium overlaid with an insulative layer, for example, medical grade polyurethane or silicone, except where electrode 112 is formed as an exposed portion of capsule 101. An hermetic feedthrough assembly (not shown), such as any known to those skilled in the art, couples electrode 111 to pulse generator 103 contained within capsule 103.

With further reference to FIGS. 1A-B, those skilled in the art will appreciate that system 100, via electrodes 111, 112, has the capability to sense intrinsic ventricular depolarization (i.e. R-waves) and, in the absence of the intrinsic depolarization, to apply stimulation pulses to the RV in order to create paced ventricular depolarization. Pulse generator 103 of system 100 further includes rate response sensor 135 that monitors a patient's general level of physical activity to determine an appropriate pacing rate for the patient. Examples of suitable rate response sensors include, without limitation, a force transducing sensor, such as a piezoelectric crystal like that described in commonly assigned U.S. Pat. No. 4,428,378 Anderson et al.; an AC or DC accelerometer like those described in commonly assigned U.S. Pat. No. 5,957,957 to Sheldon; and any type of physiological sensor known in the art, such as those that measure minute ventilation, QT intervals, blood pressure, blood pH, blood temperature, blood oxygen saturation etc. Numerous cardiac pacing methods that employ such RV pacing and sensing and physical activity monitoring are known in the art, for example, as disclosed in commonly assigned U.S. Pat. No. 4,428,378 (to Anderson et al.), U.S. Pat. No. 6,772,005 (to Casavant et al.), and U.S. Pat. No. 5,522,859 (to Stroebel et al.), as well as U.S. Pat. No. 5,374,281 (to Kristall et al.) and U.S. Pat. No. 6,122,546 (to Sholder et al.). Many of the aforementioned disclosures address the desire to limit the amount of pacing stimulation delivered from implantable pacemakers, particularly right ventricular stimulation in patients that have intact AV conduction (through the AV node, from the sinus node in the right atrial wall to the right and left bundle branches in the ventricular septum), in order to preserve the patient's natural conduction and increase pacemaker efficiency. However, the relatively more sophisticated pacing methods that are geared toward preserving the patient's natural conduction rely upon dual chamber sensing as these methods were developed in concert with the evolution of pacemaker systems from single chamber to dual chamber. Thus, there is a need for new cardiac pacing methods that preserve natural conduction and increase system efficiency for single chamber implantable pacing systems, of either the traditional type or the relatively compact type, like that shown in FIGS. 1A-B.

SUMMARY

Embodiments of the present invention include single chamber pacing systems that employ the methods disclosed. According to some methods of the present invention, an offset rate for pacing is established according to a predetermined decrement of either a baseline rate or a greater of the baseline rate and an intrinsic rate, wherein the baseline rate is established according to input from one or more rate response sensors. Pacing stimulation is applied when necessary to maintain the offset rate (for example, as determined via sensing for intrinsic ventricular depolarization), until x of y successive events (x>1 and y≥x) are paced events, at which time the offset rate is switched to the baseline rate and pacing stimulation at the baseline rate is applied over a predetermined period of time. According to some methods, the predetermined period of time may be shortened in response to the detection of intrinsic events occurring at a rate greater than the baseline rate. At the end of the predetermined period of time, sensing for intrinsic events resumes, and, according to some preferred methods, if an intrinsic event is not immediately detected, within the time interval necessary to at least maintain the offset rate, the rate is switched back to the baseline rate for pacing over an increased period of time.

According to some preferred methods, the predetermined decrement may be increased to establish an even lower offset rate, when a preference rate is established in between the baseline and offset rates. The establishment of the preference rate is associated with inclusion of another switching criterion in addition to the aforementioned x of y criterion. When the preference rate is employed, a switch from the offset rate to the baseline rate occurs, even if the aforementioned x of y criterion is not met, when successive intrinsic events meet another predetermined criterion with respect to the preference rate, for example, when a detected measure of central tendency for successive intrinsic events, over a predetermined interval, falls below the preference rate.

BRIEF DESCRIPTION OF THE DRAWINGS

The following drawings are illustrative of particular embodiments and methods of the present invention and therefore do not limit the scope of the invention. The drawings are not to scale (unless so stated) and are intended for use in conjunction with the explanations in the following detailed description. Methods of the present invention will hereinafter be described in conjunction with the appended drawings wherein like numerals denote like elements.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1A:
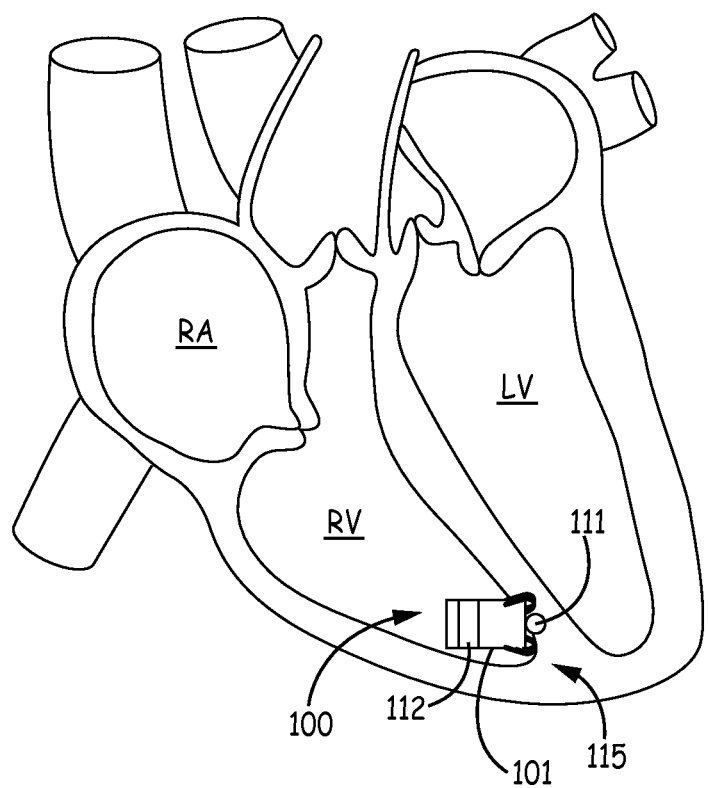
FIGS. 1A-B are schematics providing context for methods of the present invention.
Figure 1B:
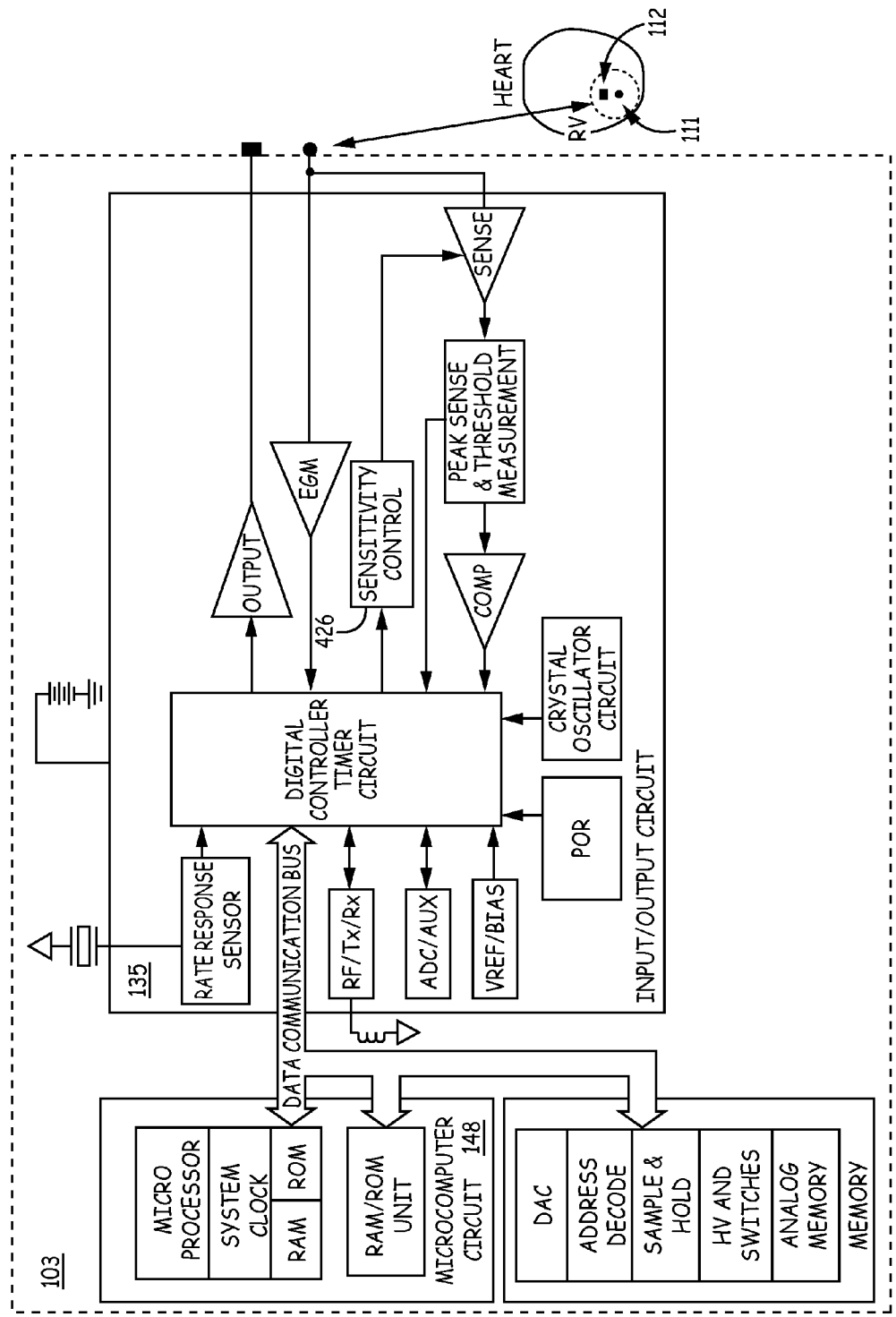

With reference to FIG. 1A, pacing system 100 is shown wholly implanted against an endocardial surface within the right ventricle RV for right ventricular pacing and stimulation. However, methods of the present invention may be employed by any single chamber pacing system (either the traditional type or the relatively compact type) when implanted endocardially or epicardially, for either ventricular pacing and sensing, or atrial pacing and sensing (left or right chambers). Thus the term "intrinsic events" used in the following description can designate either ventricular or atrial depolarization signals. FIG. 1B is a block diagram of the electrical components of pulse generator 103 including a microcomputer circuit 148, known to those skilled in art, wherein a microprocessor element thereof may be preprogrammed to direct pulse generator 103 to execute any of methods disclosed herein. Although not shown, an appropriate implantable battery power source is preferably included within capsule 101 to power the electrical components of pulse generator 103.

Figure 2:
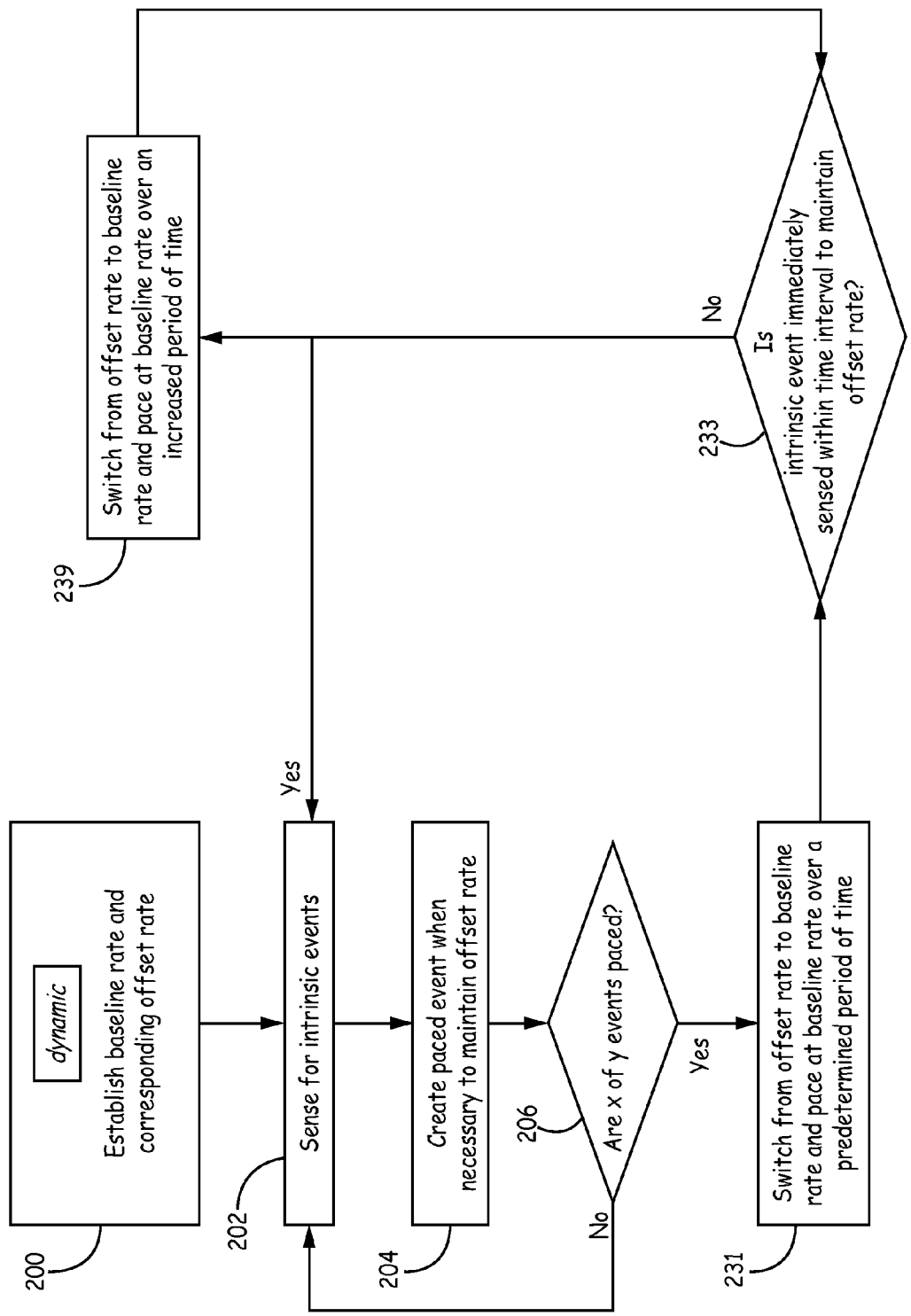
FIG. 2 is a flowchart outlining some methods of the present invention.

FIG. 2 is a flowchart outlining some methods of the present invention, whereby baseline and offset rates, established via dynamic input from rate response sensor 135 and electrodes 111, 112, are utilized by pacing system 100 to provide adequate pacing support to a patient while minimizing any unnecessary pacing stimulation. In a first step 200 of the outlined method, the baseline rate is dynamically established by means of input from rate response sensor 135; that is, the rate response sensor, which may include one or more activity or physiologic sensors, such as those described above, tracks a level of patient activity and provides input concerning an appropriate pacing rate to support the patient at any given time, which appropriate rate is designated as the baseline rate. Step 200 further includes establishment of the corresponding offset rate, which is lower than the baseline rate and generally tracks the baseline rate at a predetermined decrement thereof, according to some methods. However, according to some alternate methods, if an intrinsic rate, as sensed by electrodes 111, 112, exceeds the baseline rate, the offset rate is established by a predetermined decrement of the sensed intrinsic rate. According to some methods, the predetermined decrement may be absolute or percentage based, according to rate (bpm) or interval (ms), or any combination thereof; some examples are presented in Table 1. In Table 1, the term 'tracked rate' is used to generically designate either the baseline rate or the intrinsic rate, depending upon the method employed—baseline rate, if the first of the aforementioned methods is employed or if the baseline rate exceeds the intrinsic rate, when the latter, alternative method is employed; and intrinsic rate, if the latter method is employed and the intrinsic exceeds the baseline.

TABLE 1

| | Offset Rate when tracked rate = 60 beats per minute (1000 ms intervals) | Offset Rate when tracked rate = 100 beats per minute (600 ms intervals) | Offset Rate when tracked rate = 175 beats per minute (342 ms intervals) |
| --- | --- | --- | --- |
| Predetermined rate decrement | | | |
| subtract 10 bpm | 50 bpm | 90 bpm | 165 bpm |
| subtract 12 bpm | 48 bpm | 88 bpm | 163 bpm |
| subtract 15 bpm | 45 bpm | 85 bpm | 160 bpm |
| subtract 20 bpm | 40 bpm | 80 bpm | 155 bpm |
| subtract 25% bpm | 45 bpm | 75 bpm | 131 bpm |
| add 25% ms | 48 bpm (1250 ms intervals) | 80 bpm (750 ms intervals) | 140 bpm (427 ms interval) |
| add 25% ms-50 ms | 50 bpm (1200 ms intervals) | 85 bpm (700 ms intervals) | 160 bpm (377 ms intervals) |
| add 30% ms | 46 bpm (1300 ms intervals) | 76 bpm (780 ms intervals) | 134 bpm (445 ms intervals) |

Note:
the last three rate decrements are presented in terms of beat-to-beat intervals in units of milliseconds.

In steps 202 and 204 of FIG. 2, sensing intrinsic events and only applying pacing stimulation to create paced events that maintain the lower offset rate allows the patient's natural conduction to persist until such time that the method determines pacing stimulation is necessary to support the patient. According to decision point 206 of FIG. 2, this time is reached when x of y successive events are paced events, wherein x is always greater than one and y may be equal to x or greater than x. When this x of y criterion is met, the pacing rate switches from the offset rate to the baseline rate for pacing over a predetermined period of time, according to step 231. Two examples of the x of y switching criterion are shown in FIGS. 3A-B.

Figure 3A:
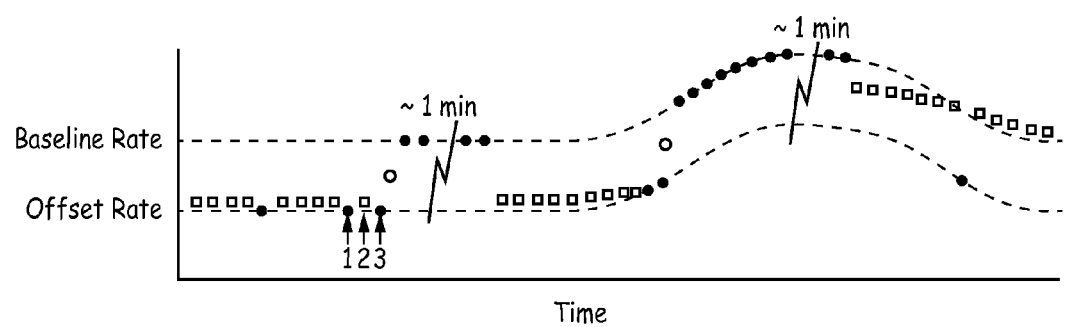
FIGS. 3A-B are plots illustrating examples that correspond to the flow chart of FIG. 2.
Figure 3B:
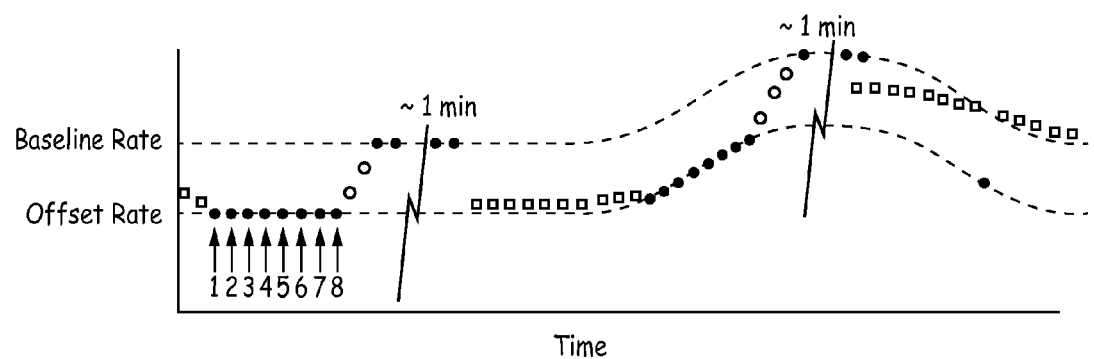

FIGS. 3A-B are plots of rate vs. time wherein open boxes represent intrinsic events, closed circles represent paced events, and dashed lines denote the established baseline and offset rates. (Note that, according to the aforementioned alternate methods, the baseline rate in the Figures could alternately be the intrinsic rate, if and when the intrinsic rate is greater that the baseline rate.) FIG. 3A illustrates a switching criterion of x=2 and y=3 and FIG. 3B illustrates a switching criterion of x=8 and y=8. FIGS. 3A-B further illustrate a predetermined period of time of approximately one minute, over which pacing stimulation is applied at the baseline rate. However, according to some methods, if, before the end of the predetermined period of time, intrinsic events occurring at a greater rate are detected, the pacing stimulation is aborted, thereby effectively shortening the predetermined period of time. In either case, at the end of the predetermined period, if intrinsic events are immediately detected at a rate that at least corresponds to the offset rate, sensing continues per step 202 of FIG. 2, as shown in FIGS. 3A-B. Alternately, with reference to decision point 233 of FIG. 2, if, at the end of the predetermined period of time of pacing, an intrinsic event is not immediately detected within the time interval necessary to at least maintain the offset rate, so that a paced event is created for maintenance of the offset rate, the method switches the rate back to the baseline rate for pacing over an increased period of time, per step 239. Although not shown in FIG. 2, the method preferably includes a maximum limit on this increased period of time, for example, sixteen hours, so that subsequent increased periods of time, if necessary, do not exceed maximum.

Figure 4:
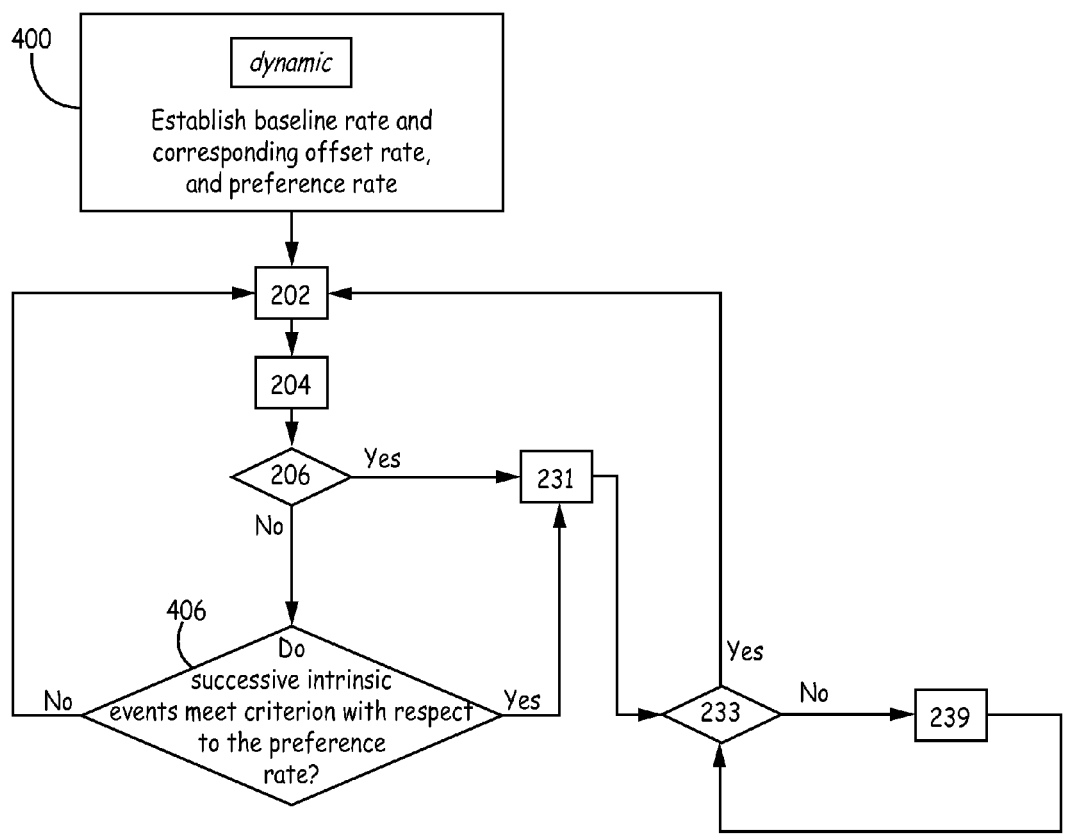
FIG. 4 is a flowchart outlining some alternate methods of the present invention.

FIG. 4 is a flowchart modified from that shown in FIG. 2 to outline yet further methods of the present invention. The methods outlined in FIG. 4 differ from those outlined in FIG. 2 in that an additional rate, called the preference rate, is established, per step 400, and an additional switching criterion, corresponding to the preference rate is included at decision point 406. According to methods outlined in FIG. 4, even if x of y paced events are not detected, the switch, per step 231, may be made, if the criterion at decision point 406 is met, for example as illustrated in the plot FIG. 5.

Figure 5:
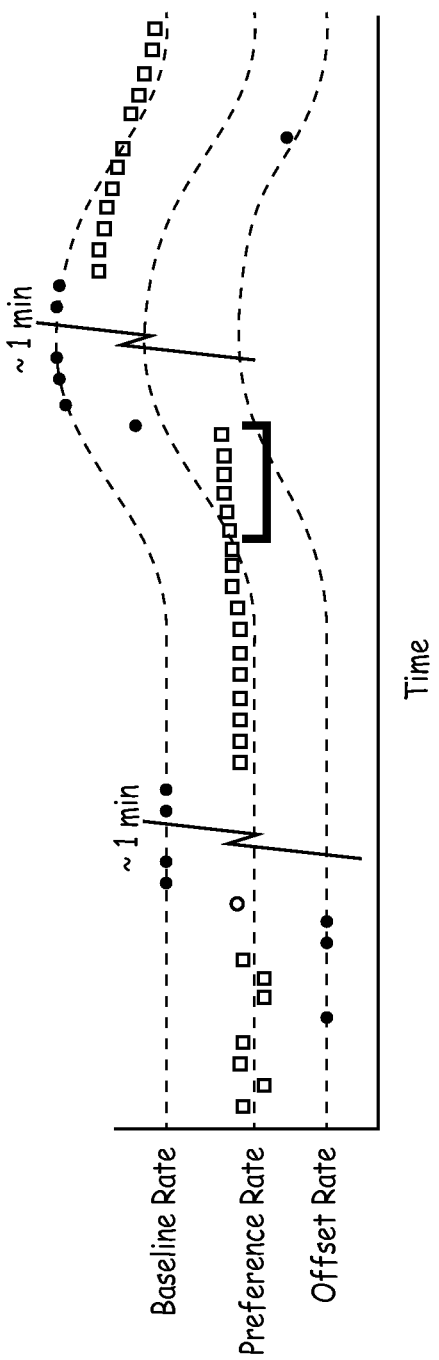
FIG. 5 is a plot illustrating an example that corresponds to the flow chart of FIG. 4.

FIG. 5 is a plot of rate vs. time, wherein open boxes represent intrinsic events and closed circles paced events, like the plots of FIGS. 3A-B. The dashed lines in FIG. 5 denote the established baseline, preference and offset rates. The preference rate, which is between the baseline rate and the offset rate allows for a greater predetermined decrement, or a lower offset rate, without sacrificing pacing support in the event of chronotropic incompetence, which, according to decision point 406 of FIG. 4, corresponds with the successive intrinsic events meeting a predetermined criterion with respect to the preference rate over a predetermined interval, as designated by the bracket in FIG. 5. This criterion may be x of y intrinsic events (x>1 and y≥x) falling below the preference rate, although remaining above the offset rate, or some measure of central tendency, like mean, median or mode, of successive intrinsic events over a predetermined interval being less than the preference rate, although greater than the offset rate. Establishing the lower offset rate with the protection of the preference rate, according to the methods of FIG. 4, can allow normal/physiological micro rate changes that temporarily slow the intrinsic heart rate (i.e. those associated with respiration changes) to be tolerated without creating paced events. With reference back to Table 1, the same exemplary means used to establish the offset rate may be used to establish the preference rate, according to some methods.

Finally, with further reference to the plots of FIGS. 3A-B and 5, according to some methods, at least one pacing stimulation pulse at a rate between either the offset rate or the preference rate and the baseline rate (as designated by grey circles) is applied just prior to the switch to the baseline rate. Whether or not such transition, or "rate smoothing" pulses are applied, and the number of pulses applied depends upon the magnitude of the difference between the two rates at the time the switch is made.

In the foregoing detailed description, the invention has been described with reference to specific methods. However, it may be appreciated that various modifications and changes can be made without departing from the scope of the invention as set forth in the appended claims.

We claim:

1. A single chamber cardiac pacing system configured to be wholly implanted in a patient's heart, the system including:
   implantable electrodes;
   a pulse generator coupled to the electrodes;
   one or more rate response sensors;
   means for establishing a baseline rate for pacing stimulation according to input from the one or more rate response sensors;
   means for establishing an offset rate for pacing stimulation, the offset rate having a magnitude that is one of:
      lower than the baseline rate, wherein a change in the baseline rate is generally tracked by the offset rate such that a difference between the baseline rate and the offset rate remains substantially constant over time in response to the baseline rate being less than or equal to an intrinsic rate, and
      lower than an intrinsic rate, wherein a change in the intrinsic rate is generally tracked by the offset rate such that a difference between the intrinsic rate and the offset rate remains substantially constant over time in response to the intrinsic rate being greater than the baseline rate;
   means for sensing for intrinsic cardiac events by means of the implanted electrodes;
   means for applying a pacing stimulation pulse by means of the implanted electrodes, responsive to an intrinsic event not being sensed within a time interval necessary to at least maintain the offset rate, the applied pacing stimulation pulse creating a paced event to maintain the offset rate;
   means for switching from the offset rate to the baseline rate and triggering pacing at the baseline rate over a predetermined period of time, responsive to x of y successive cardiac events being paced events, x being greater than one and y being greater than or equal to x; and wherein the intrinsic heart rate is determined according to prior sensed intrinsic events.

2. The system of claim 1, wherein the predetermined period of time is shortened in response to detection of intrinsic events occurring at a rate that is greater than the baseline rate.

3. The system of claim 1, further comprising means for:
   establishing a preference rate that falls between the baseline rate and the offset rate; and
   wherein the switching means switches from the offset rate to the baseline rate and triggers pacing at the baseline rate over the predetermined period of time, responsive to the rates of successive intrinsic events, over a predetermined interval, even if greater than the offset rate, meeting a criterion with respect to the preference rate, the criterion being one of: x of y successive intrinsic events falling below the preference rate over the predetermined interval, x being greater than one and y being greater than or equal to x; and a measure of central tendency of the rates of successive intrinsic events falling below the preference rate over the predetermined interval.

4. The system of claim 3, wherein the preference rate is established according to a predetermined decrement of the baseline rate, the predetermined decrement being one or a combination of: a fixed beats per minute decrement, a percentage beats per minute decrement, a fixed interval increment, and a percentage interval increment.

5. The system of claim 3, further wherein the switching means triggers at least one pacing stimulation pulse at a rate between the preference rate and the baseline rate, responsive to the rates of successive intrinsic events meeting the criterion with respect to the preference rate, and just prior to the corresponding switch to the baseline rate.

6. The system of claim 3, wherein, at the end of the predetermined period of time, responsive to an intrinsic event not being detected within the time interval necessary to at least maintain the offset rate, the switching means switches back to the baseline rate and pacing at the baseline rate over another predetermined period of time that is increased from the previous predetermined period.

7. The system of claim 1, wherein the offset rate is established according to a predetermined decrement of the baseline rate, the predetermined decrement being one or a combination of: a fixed beats per minute decrement, a percentage beats per minute decrement, a fixed interval increment, and a percentage interval increment.

8. The system of claim 1, wherein the switching means triggers at least one pacing stimulation pulse at a rate between the offset rate and the baseline rate, just prior to the switch to the baseline rate.

9. The system of claim 1, wherein x equals two and y equals three or x and y both equal eight.

10. The system of claim 1, wherein the predetermined period of time is equal to approximately one minute.

11. The system of claim 1, wherein the substantially constant difference over time is maintained by decrementing the offset rate by a value that corresponds to the change in magnitude of the baseline rate.

12. The system of claim 1, wherein the substantially constant difference over time is maintained by incrementing the offset rate by a value that corresponds to the change in magnitude of the baseline rate.

13. The system of claim 1, wherein the offset rate is established according to a predetermined decrement of one of: the baseline rate; and a greater of the baseline rate and an intrinsic heart rate.

* * * * *